United States Patent
Xu et al.

(10) Patent No.: US 7,737,690 B2
(45) Date of Patent: Jun. 15, 2010

(54) SYSTEM AND METHOD FOR AMPLITUDE REDUCTION IN RF PULSE DESIGN

(75) Inventors: Dan Xu, Springfield, IL (US); Kevin F. King, Menomonee Falls, WI (US)

(73) Assignee: General Electric Company, Schenectady, NY (US)

( * ) Notice: Subject to any disclaimer, the term of this patent is extended or adjusted under 35 U.S.C. 154(b) by 96 days.

(21) Appl. No.: 11/750,478

(22) Filed: May 18, 2007

(65) Prior Publication Data

US 2008/0284439 A1 Nov. 20, 2008

(51) Int. Cl.
*G01V 3/00* (2006.01)
(52) U.S. Cl. .................................................. 324/307
(58) Field of Classification Search ......... 324/300–322; 600/410–435
See application file for complete search history.

(56) References Cited

U.S. PATENT DOCUMENTS

| | | | |
|---|---|---|---|
| 5,105,152 A | | 4/1992 | Pauly |
| 5,313,163 A | | 5/1994 | Hardy et al. |
| 5,402,067 A | * | 3/1995 | Pauly et al. ................. 324/307 |
| 6,313,630 B1 | * | 11/2001 | Ganin et al. ................. 324/312 |
| 6,937,015 B2 | * | 8/2005 | Heid ........................... 324/307 |
| 7,030,611 B2 | * | 4/2006 | Sakakura .................... 324/318 |
| 7,046,003 B2 | * | 5/2006 | Hargreaves et al. ......... 324/307 |
| 2007/0236216 A1 | * | 10/2007 | Pipe ............................ 324/307 |

OTHER PUBLICATIONS

S. M. Conolly, D. G. Nishimura, and A. Macovski, "Variable-rate selective excitation", J. Magn. Reson., vol. 78, pp. 440-458, 1988.
K. F. King, T. K. F. Foo, and C. R. Crawford, "Optimized gradient waveforms for spiral scanning", Magn. Reson. Med., vol. 34, pp. 156-160, 1995.
G. H. Glover, "Simple analytic spiral k-space algorithm", Magn. Reson. Med., vol. 42, pp. 412-415, 1999.
C. Salustri, Y. Yang, J. H. Duyn, and G. H. Glover, "Comparison between analytical and numerical solutions for spiral trajectory in 2D k-space", in Proc. 5th Ann. Meet. Intl. Soc. Mag. Reson. Med., p. 1813, Vancouver, Canada, Apr. 1997.
J. H. Duyn, and Y. Yang, "Fast spiral magnetic resonance imaging with trapezoidal gradients", J. Magn. Reson., vol. 128, pp. 130-134, 1997.

* cited by examiner

*Primary Examiner*—Brij B Shrivastav
*Assistant Examiner*—Dixomara Vargas
(74) *Attorney, Agent, or Firm*—Ziolkowski Patent Solutions Group, SC (57) ABSTRACT

A system and method are provided for adjusting RF pulses and gradient waveforms to reduce $B_1$ field magnitude in MR imaging sequences. When an RF pulse is presented which has a high amplitude segment that would exceed a maximum $B_1$ magnitude, the system and method provided herein can apply a variable slew rate design technique. A slew rate of at least one gradient waveform can be varied to reduce a $B_1$ field magnitude during transmission of the high amplitude segment of the RF pulse. By controlling the slew rate of gradient waveforms for non-Cartesian k-space trajectories according to a calculated maximum allowable slew rate function, embodiments of the system and method can, in effect, reduce gradient amplitude.

20 Claims, 8 Drawing Sheets

CONSTANT |S|, $S°_{max}$ =14500

$G_x$ FOR CONSTANT SLEW RATE SPIRAL, $T_s$ = 3.3 msec

RF PULSE WITH $G_x$
MAX. AMPLITUDE = 0.69 (Gauss)

FIG. 6

CONSTANT |S| SCALED FROM |S|,
$S°_{max} = 1611$ $G_x$ FOR SCALED CONSTANT
SLEW RATE SPIRAL, $T_s = 9.8$ msec RF PULSE WITH $G_x$
MAX. AMPLITUDE = 0.26 (Gauss)

SYSTEM AND METHOD FOR AMPLITUDE REDUCTION IN RF PULSE DESIGN

BACKGROUND OF THE INVENTION

The present invention relates generally to magnetic resonance (MR) imaging, and more specifically, to a system and method which provide for $B_1$ amplitude reduction in RF pulse design. By adjusting peak or high amplitude portions of an RF pulse and the corresponding gradient waveforms, overall RF transmit power can be reduced, and the specific absorption rate (SAR) of the pulse can be controlled. Such a reduction in amplitude can be extended for non-linear k-space trajectories, such as for spiral and non-uniform trajectories.

MR imaging in general is based upon the principle of nuclear magnetic resonance. When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field, such as a $B_1$ excitation field, which is in the x-y plane and which is near the Larmor frequency, the net aligned moment, or "longitudinal magnetization", $M_z$, may be rotated, or "tipped", into the x-y plane to produce a net transverse magnetic moment $M_t$. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received NMR signals are digitized, encoded, and processed to acquire a set of data known as k-space data. This data is then used to reconstruct an image using one of many well known reconstruction techniques. The shape of the magnetic field gradient waveforms contributes to the manner and order in which the k-space data is acquired, also known as a k-space trajectory.

During a transmit sequence, an MR system will also transmit RF pulses having specially designed frequencies and amplitude profiles while the magnetic field gradients are being applied. For example, an MR system might transmit an excitation pulse at a particular frequency and amplitude for a particular time, in order to induce a net transverse magnetization in nuclei of a scan subject. Subsequent pulses transmitted by the system may have the same or a similar frequency, but might have different gain, amplitude, or duration attributes to cause a different change in magnetization (or "flip angle"). In addition, the attributes of RF pulses can be adjusted such that only spins within a given 2D or 3D portion of a scan subject are affected. This is useful in such techniques as reduced field of view imaging or spatially-selective imaging. Thus, in general, the particular shapes of the RF pulses in a transmit sequence are varied to manipulate the net magnetization in nuclei of scan subject.

Presently, RF pulses are designed using a variety of techniques, via both direct and approximation approaches. A few exemplary design techniques include the Shinnar-LeRoux technique, the small tip angle (STA) approximation, the linear class large tip angle (LCLTA) approximation, techniques based upon EPI trajectories, and other determinations based upon the Bloch equations. It is often the case, however, that these RF pulse design techniques produce RF pulses having profiles with one or more segments of undesirably high amplitudes. For example, a complex RF pulse shape associated with a 2D or 3D spatially-selective RF pulse can sometimes have a peak amplitude segment that exceeds desired SAR limits. Additionally, such an RF pulse might have high amplitude portions which result in an RF transmission power exceeding the maximum achievable transmission power of a given system. A peak amplitude segment may often be associated with the portion of the pulse corresponding to near the origin of the excitation k-space. Therefore, it has been appreciated that accommodation should be made to improve the transmission characteristics of these portions of RF pulses.

One way to reduce peak RF amplitude and SAR is to reduce the amplitude of the entire RF pulse and proportionately lengthen the pulse, while performing the same operation to the gradient waveforms, thereby producing the same magnetization or flip angle profiles. For example, the amplitude of an RF pulse could be quartered, and the duration quadrupled. However, such an approach may be deemed impracticable in many circumstances, since the result could be an RF pulse with a rather long duration. Longer durations of RF pulses can cause reduced image quality due to relaxation, off-resonance frequency, etc.

Another type of pulse modification which may limit high amplitude or high transmit power portions of an RF pulse design is known as the variable rate selective excitation (VERSE) technique. Implementations of the VERSE technique "time-dilate" the local shape of RF pulses and gradient waveforms to reduce peak $B_1$ amplitude while satisfying such hardware constraints as maximum gradient amplitude and slew-rate. By using the time-dilation function, the VERSE technique provides more practical control over peak $B_1$ amplitude and SAR, as compared to conventionally designed pulses or stretched pulses. That is, VERSE pulses are typically employed as a technique for reducing peak power over a high amplitude portion of a pulse. However, to date, the VERSE technique has been known to be implementable only for common, single dimensional (1D) spatially-selective RF pulses with constant gradients.

Generally, VERSE pulses are RF pulses which have been derived from a pre-existing, conventionally designed RF pulse. The conventionally designed RF pulse can be produced by any of a variety of design methods for a desired flip angle, duration, bandwidth, etc. Where a portion of the RF pulse is undesirably high in amplitude, the VERSE technique can be applied in a post-design processing to proportionately reduce and lengthen only the undesirably high portion of the RF pulse. In turn, the corresponding portion of the slice-select gradient waveform is similarly reduced and lengthened, to maintain the desired slice selection.

Figure 1:
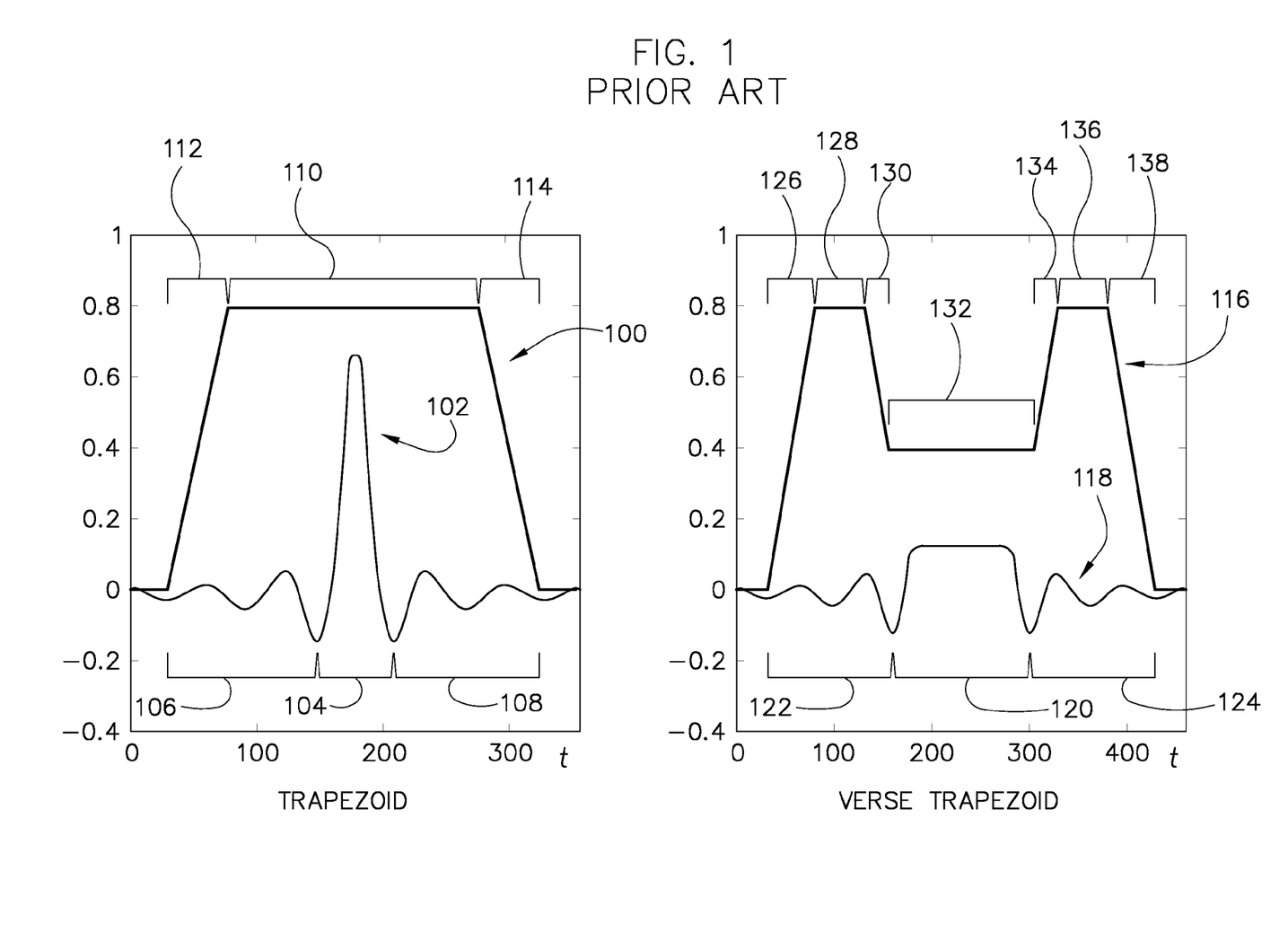
FIG. 1 is a comparison graph of a typical RF pulse and a VERSE pulse.

As shown in FIG. 1, an exemplary constant magnitude slice-select gradient waveform 100 may, in implementation, take the general form of a trapezoid for transmission with an exemplary 1D RF pulse. The associated RF pulse 102 may generally be a sinc pulse. The gradient waveform is designed having a first ramp 112 increasing to a constant amplitude segment 110, then followed by a decreasing ramp 114. The RF pulse 102 has a first sidelobe 106, a mainlobe 104 having a higher amplitude, and a second side lobe 108. According to the VERSE technique, pulse 102 and waveform 100 may be adjusted to control SAR during the mainlobe 104 of the RF pulse 100.

Generally, to reduce peak RF amplitude and control SAR using the VERSE technique, the high amplitude segment 104 of the RF pulse can be reshaped, after the pulse 102 was initially designed. Thus, a VERSE RF pulse 118 is generally characterized by a lengthened or stretched mainlobe segment 120, while the sidelobes 122, 124 remain relatively unchanged. Thus, the peak RF amplitude is reduced, and the RF power from the peak segment 104 of the conventionally designed pulse 102 is spread over a longer segment 120 in the VERSE pulse 118. The stretched segment 118 of the VERSE RF pulse 118 is then transmitted in the presence of a lengthened, reduced slice select (Gz) gradient 116, to maintain the net desired flip angle, while controlling the effective $B_1$ field and SAR. Thus, the center portion 132 of the gradient waveform corresponding in time to the stretched mainlobe 120 has been reduced and stretched. The remaining portions 128 and 136 of the constant amplitude section of the gradient pulse 116, as well as the ramps 126 and 138 remain the same. Thus, the VERSE technique provides a post-design way to control SAR without lengthening the duration of an entire pulse.

However, the VERSE technique is not presently known to be directly applicable for sequences that use spiral or other non-linear or non-uniform k-space trajectories, such as those used with two dimensional (2D) spatially-selective RF pulses. One challenge in applying VERSE to non-Cartesian k-space trajectories (e.g., a spiral) is that the time dilation function and its derivatives get propagated, via the chain rule of differentiation, into the gradient and slew-rate expressions. Therefore enforcing gradient amplitude constraints and slew-rate constraints would lead to complicated differential inequalities, which would be difficult to solve.

Figure 2:
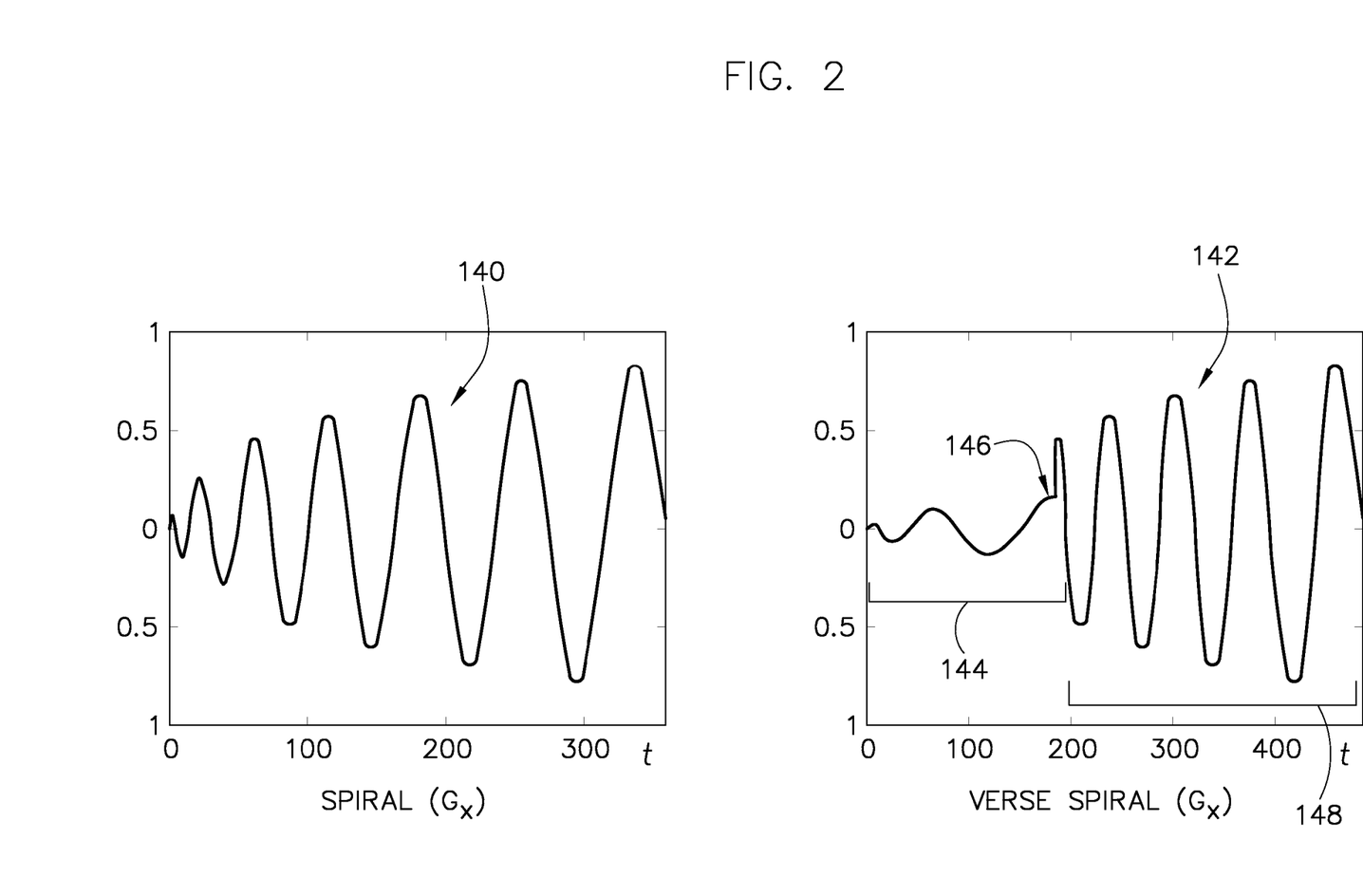
FIG. 2 is a comparison graph of a typical frequency-encoding gradient for a spiral trajectory and a frequency-encoding gradient for a VERSE spiral trajectory.

Another challenge in directly applying VERSE to non-Cartesian trajectories is the limitations on waveform shapes imposed by hardware constraints. To illustrate, FIG. 2 depicts an exemplary frequency encoding (Gx) gradient waveform 140 to implement a non-Cartesian, spiral k-space trajectory. If the VERSE technique, as described above, was directly applied to waveform 140, the portion 144 corresponding to a high amplitude RF segment would be stretched in duration and decreased in amplitude, while the remainder 148 of the pulse would be unchanged. However, as shown, such a technique would create a sharp change or discontinuity 146 in the waveform where the two segments 144, 148 meet. Such a discontinuity 146 is not known to be implementable by gradient coil assemblies, due to slew rate constraints. As such, the advantages of a VERSE-type SAR reduction have not been used for non-uniform or non-Cartesian k-space trajectories.

It would therefore be desirable to have a system and method capable of reducing $B_1$ power during a portion of an RF pulse designed according to a non-Cartesian k-space trajectory. It would be further desirable for embodiments of such a system and method to quickly and efficiently calculate adjustments to existing RF pulse profiles and gradient waveforms and to maintain a relatively short transmit duration of the pulses.

BRIEF DESCRIPTION OF THE INVENTION

Embodiments of the present invention provide for the design and implementation of an MR system which overcomes the aforementioned drawbacks. In particular, various embodiments of the invention produce adjusted RF pulses and/or gradient waveforms which can reduce $B_1$ power, and, as a consequence, can reduce SAR. For RF pulses defined according to non-Cartesian k-space trajectories, embodiments of the invention can adjust the oscillating gradient waveforms to effectuate the $B_1$ power reduction without creating non-implementable discontinuities in the waveforms.

Therefore, in accordance with one aspect of the invention, an MRI system includes a plurality of gradient coils positioned about a bore of a magnet, an RF transceiver system and switch, a pulse module, an RF coil assembly, and a controller. The RF transceiver system and RF switch are controlled by the pulse module to transmit RF signals to the RF coil assembly to acquire MR images. The controller is operatively connected to the pulse module, and is programmed to determine an RF pulse profile and identify a high amplitude segment thereof. The controller is further programmed to design at least one gradient waveform, in which a slew rate of the waveform is varied to reduce $B_1$ field magnitude during transmission of the high amplitude segment of the RF pulse profile. The control is programmed to then output the RF pulse profile for transmission by the RF coil assembly and output the at least one gradient waveform for transmission by at least one of the plurality of gradient coils.

In accordance with another aspect of the invention, a method is provided for reducing RF pulse amplitude. The method includes the steps of designing a gradient waveform to implement a non-Cartesian k-space trajectory and determining a maximum slew rate function to vary the slew rate of the gradient waveform during at least part of the slew-rate limited segment of the waveform. The method then includes re-designing the gradient waveform according to the maximum slew rate function. The re-designed gradient waveform is the played out with an RF pulse to acquire MR image data. The MR image data is, at least temporarily, stored in memory.

In accordance with a further aspect of the invention, a set of instructions are stored onto a computer-readable storage medium. The instructions, when executed by a computer, cause the computer to perform a number of actions. The computer determines an allowable slew rate functions and re-designs at least one oscillating gradient waveform according to the allowable slew rate function. The computer then outputs the oscillating gradient waveform and an RF pulse profile for transmission in an imaging sequence. The instructions further cause the computer to reconstruct and display an image based upon MR data resulting from the imaging sequence.

Various other features and advantages will be made apparent from the following detailed description and the drawings.

BRIEF DESCRIPTION OF THE DRAWINGS

The drawings illustrate embodiments presently contemplated for carrying out the invention.

In the drawings.

DETAILED DESCRIPTION OF THE PREFERRED EMBODIMENT

Figure 3:
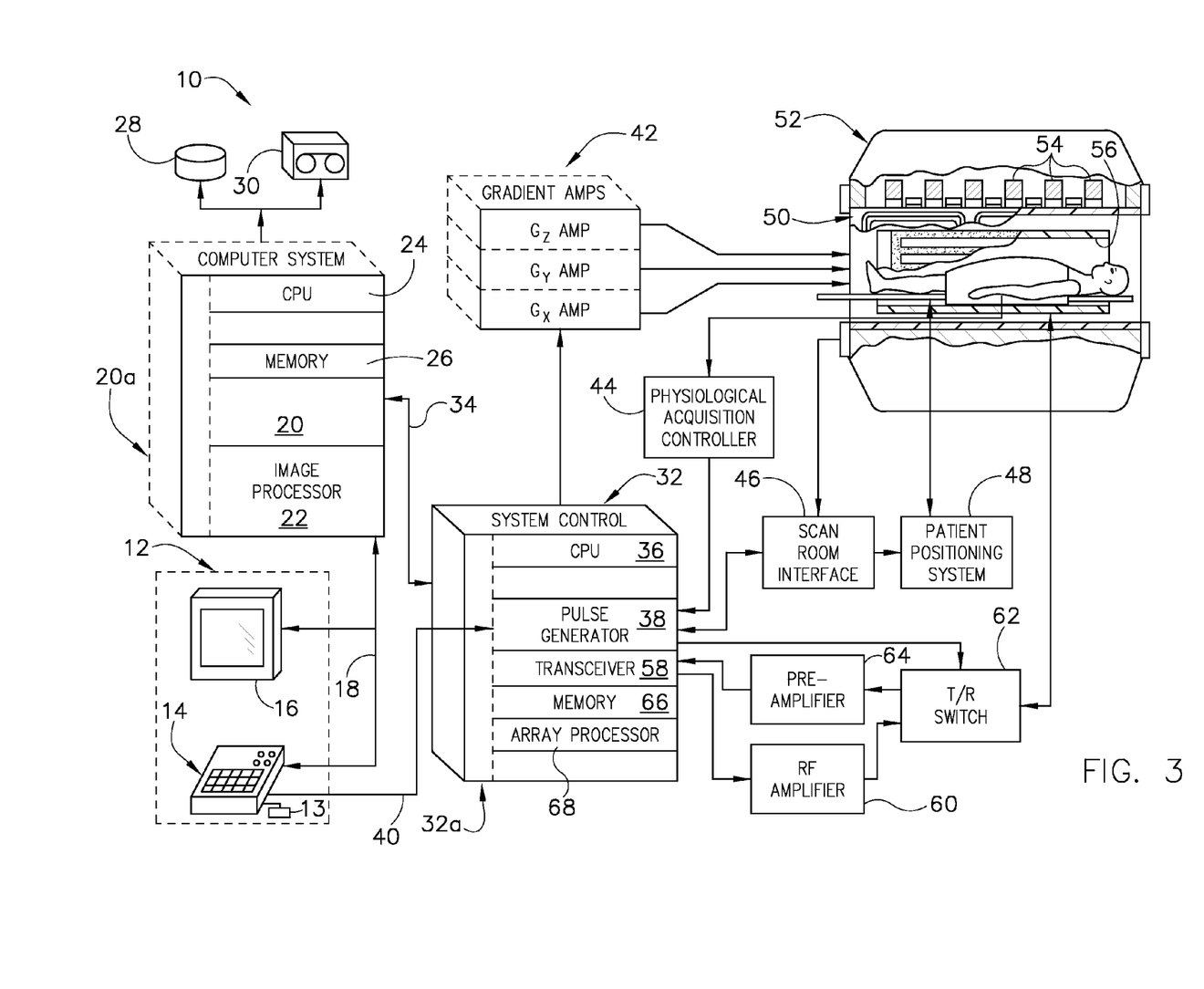
FIG. 3 is a schematic block diagram of an MR imaging system for use with embodiments of the present invention.

Referring to FIG. 3, the major components of a magnetic resonance imaging (MRI) system 10 that may incorporate embodiments of the present invention are shown. The operation of the system is controlled from an operator console 12 which includes a keyboard or other input device 13, a control panel 14, and a display screen 16. The console 12 communicates through a link 18 with a separate computer system 20 that enables an operator to control the production and display of images on the display screen 16. The computer system 20 includes a number of modules which communicate with each other through a backplane 20*a*. These include an image processor module 22, a CPU module 24 and a memory module 26, known in the art as a frame buffer for storing image data arrays. The computer system 20 is linked to disk storage 28 and removable storage 30 for storage of image data and programs, and communicates with a separate system control 32 through a high speed serial link 34. The input device 13 can include a mouse, joystick, keyboard, track ball, touch activated screen, light wand, voice control, or any similar or equivalent input device, and may be used for interactive geometry prescription.

The system control 32 includes a set of modules connected together by a backplane 32*a*. These include a CPU module 36 and a pulse generator module 38 which connects to the operator console 12 through a serial link 40. It is through link 40 that the system control 32 receives commands from the operator to indicate the scan sequence that is to be performed. The pulse generator module 38 operates the system components to carry out the desired scan sequence and produces data which indicates the timing, strength and shape of the RF pulses produced, and the timing and length of the data acquisition window. The pulse generator module 38 connects to a set of gradient amplifiers 42, to indicate the timing and shape of the gradient pulses that are produced during the scan. The pulse generator module 38 can also receive patient data from a physiological acquisition controller 44 that receives signals from a number of different sensors connected to the patient, such as ECG signals from electrodes attached to the patient. And finally, the pulse generator module 38 connects to a scan room interface circuit 46 which receives signals from various sensors associated with the condition of the patient and the magnet system. It is also through the scan room interface circuit 46 that a patient positioning system 48 receives commands to move the patient to the desired position for the scan.

The gradient waveforms produced by the pulse generator module 38 are applied to the gradient amplifier system 42 having Gx, Gy, and Gz amplifiers. Each gradient amplifier excites a corresponding physical gradient coil in a gradient coil assembly generally designated 50 to produce the magnetic field gradients used for spatially encoding acquired signals. The gradient coil assembly 50 forms part of a magnet assembly 52 which includes a polarizing magnet 54 and a whole-body RF coil 56, and may include a surface or parallel RF coil assembly 57. A transceiver module 58 in the system control 32 produces pulses which are amplified by an RF amplifier 60 and coupled to the RF coil 56 or the coil assembly 57 by a transmit/receive switch 62. The resulting signals emitted by the excited nuclei in the patient may be sensed by the same RF coil 56 or coil assembly 57 and coupled through the transmit/receive switch 62 to a preamplifier 64. The amplified MR signals are demodulated, filtered, and digitized in the receiver section of the transceiver 58. The transmit/receive switch 62 is controlled by a signal from the pulse generator module 38 to electrically connect the RF amplifier 60 to the coil 56 or the coil assembly 57 during the transmit mode and to connect the preamplifier 64 to the coil 56 or the coil assembly 57 during the receive mode.

The MR signals picked up by the RF coil 56 or the coil assembly 57 are digitized by the transceiver module 58 and transferred to a memory module 66 in the system control 32. A scan is complete when an array of raw k-space data has been acquired in the memory module 66. This raw k-space data is rearranged into separate k-space data arrays for each image to be reconstructed, and each of these is input to an array processor 68 which operates to Fourier transform the data into an array of image data. This image data is conveyed through the serial link 34 to the computer system 20 where it is stored in memory, such as disk storage 28. In response to commands received from the operator console 12, this image data may be archived in long term storage, such as on the removable storage 30, or it may be further processed by the image processor 22 and conveyed to the operator console 12 and presented on the display 16.

When RF pulses are designed for transmission by an RF coil or coil array, such as RF coil 56, pulse design techniques can sometimes produce pulses which have segments with undesirably high amplitudes. When such pulses are designed from a non-Cartesian or non-uniform k-space trajectory, it can be difficult to achieve a reduction of amplitude in the RF pulse by simply applying local stretching because a corresponding reduction in associated gradient waveforms can produce too great of a discontinuity in the gradient waveform. The sudden changes or discontinuities in the gradient waveforms often cannot be implemented due to the slew rate limits of known gradient amplifiers and coils.

Figure 4:
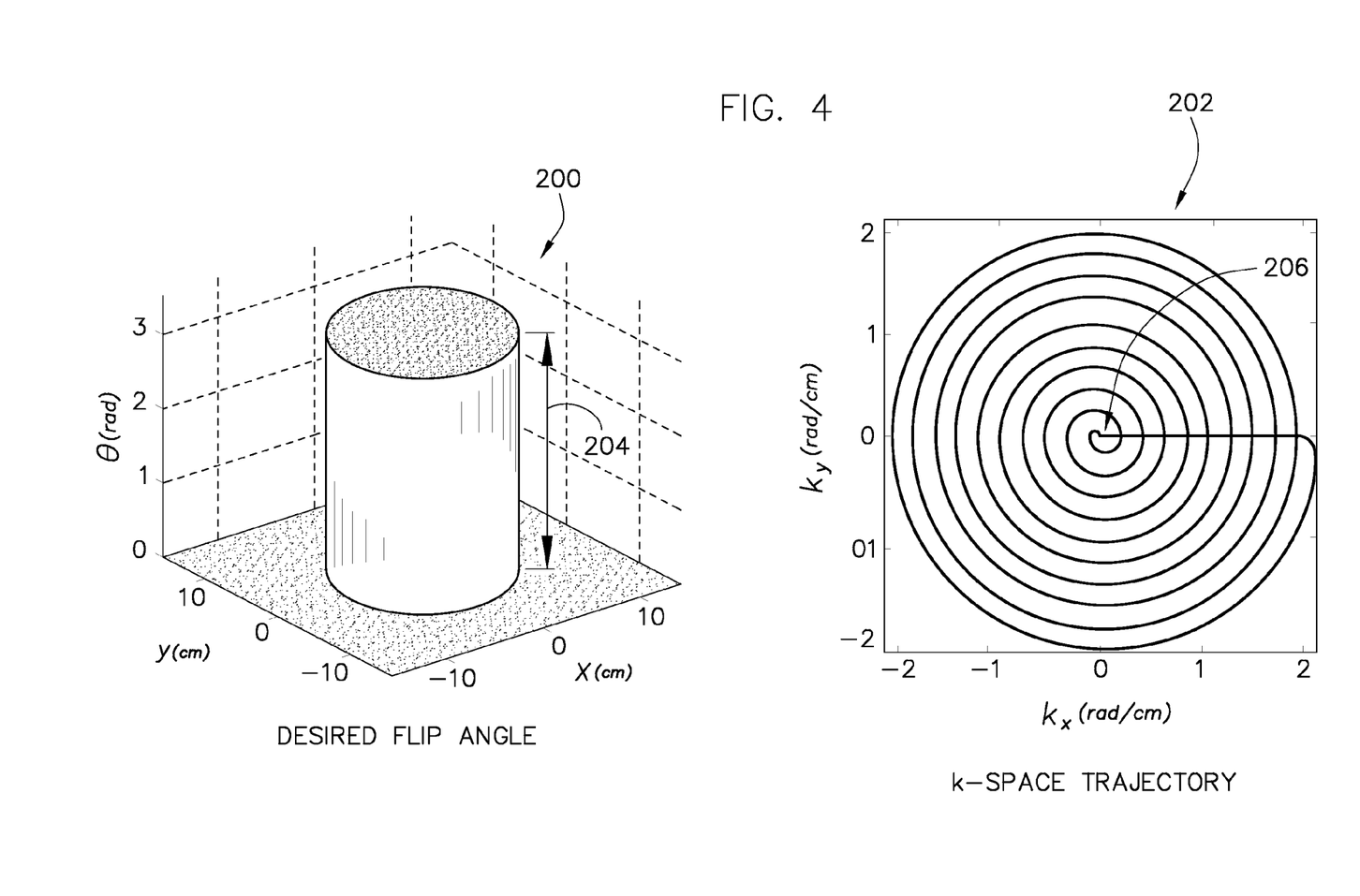
FIG. 4 is a graph of a desired flip angle profile and k-space trajectory describing an exemplary RF pulse.

When a user selects an RF pulse to be designed, the user will typically specify various characteristics of the desired pulse on a computer which will calculate an RF pulse shape achieving the desired characteristics. To illustrate, FIG. 4 depicts an exemplary magnetization or flip angle profile 200 and k-space trajectory 202 corresponding to a desired RF pulse. In some embodiments, a user may directly specify such a profile 200 and trajectory 202 as inputs for generation of an RF pulse according to an RF pulse design technique. Alternatively, a user may specify other parameters or characteristics describing the desired RF pulse, such as an overall flip angle, a field of view, an anatomy of interest, a pulse duration, a pulse sequence type, and the like. The exemplary flip angle profile 200 shown in FIG. 4 describes a pulse which is 2D spatially-selective in the x and y physical dimensions. Thus, as shown, profile 200 excites spins in a cylinder or beam extending along the z dimension 204.

As shown, k-space trajectory 202 is a spiral, inherently refocused trajectory. That is, k-space trajectory 202 begins at a center of k-space 206, spirals outwardly, and then shifts back to the center 206 to end. A trajectory such as spiral trajectory 202 is common for use with 2D spatially-selective pulses. However, it will be appreciated that embodiments of the present invention can be extended and are equally applicable for RF pulses having other dimensionalities, such as 3D spatially-selective pulses. Similarly, embodiments may also apply in trajectories which differ from that shown. For example, trajectories may be inwardly directed, outwardly directed, and may sample k-space at different resolutions. One skilled in the art will recognize that the features and advantages described herein may also extend to multiple other non-Cartesian or non-uniform k-space trajectories.

Figure 5:
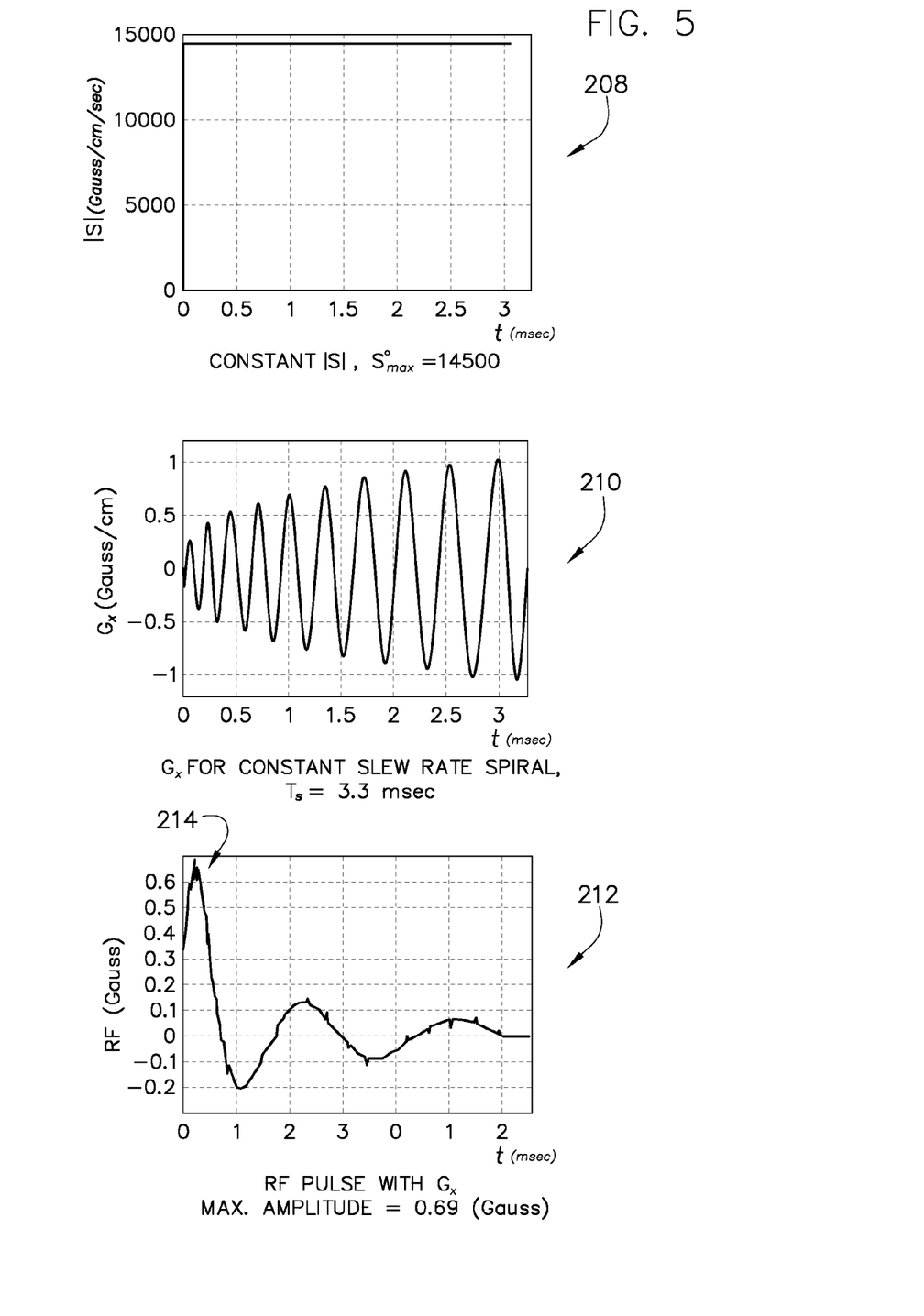
FIG. 5 is a graph of an exemplary slew rate with a corresponding frequency encoding gradient and RF waveform.

Referring now to FIG. 5, an exemplary slew rate graph 208, gradient waveform 210, and RF pulse shape 212 are shown. These waveforms are generally representative of the results, under normal conditions, from an RF pulse design technique given parameters such as described with respect to FIG. 4. That is, a $G_x$ gradient waveform 210 to implement a spiral k-space trajectory will oscillate and generally increase in amplitude over time. Likewise, a $G_y$ gradient waveform (not shown) will also oscillate and generally increase in amplitude over time.

For RF pulses which have shorter durations, such as are typical of 2D spatially-selective RF pulses designed from a spiral k-space trajectory, the corresponding x and y gradients will usually be limited only by the maximum slew rate of the MR system being used. That is, with a limited transmission period, fewer spiral turns will be achieved in the k-space trajectory, and thus the amplitude of the x and y gradient oscillations will not reach the maximum gradient field strength achievable by the MR system. Accordingly, the graph 208 of the slew rate of gradient waveform 210 is shown as constant, at the maximum achievable slew rate.

Because the k-space trajectory implemented by gradient waveform 210 is outwardly-spiraling, the portion of the RF pulse 212 corresponding to the center of k-space or positions near the center of k-space and, thus, having the highest amplitude is at the temporal beginning of the pulse 214. This level of $B_1$ amplitude is not normally achievable by existing RF power amplifiers for current commercial MRI scanners. The net SAR can also significantly exceed the desired limits.

Figure 6:
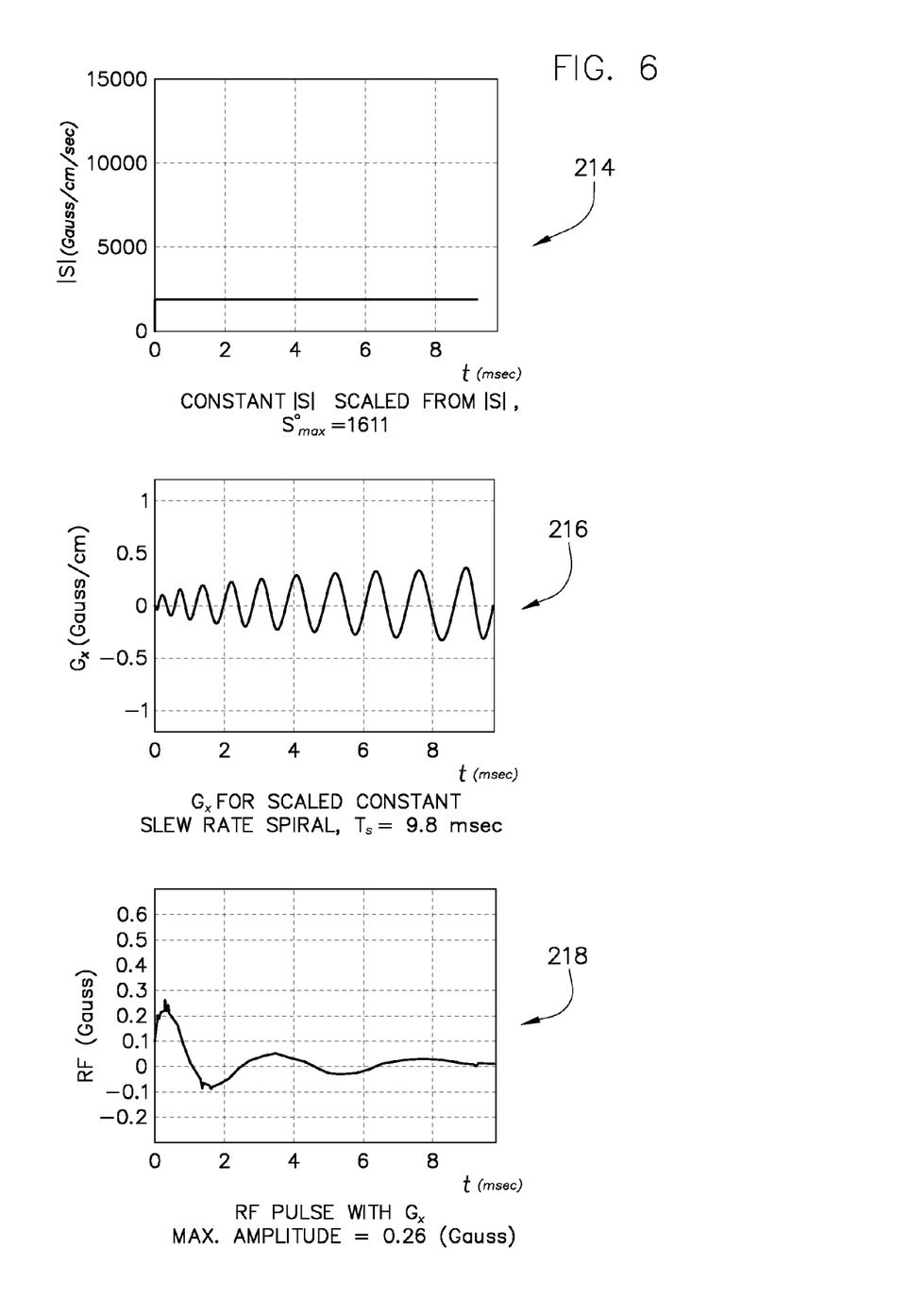
FIG. 6 is a graph of a scaled version of the slew rate, frequency encoding gradient, and RF waveform of FIG. 5.

Referring now to FIG. 6, one technique is depicted for alleviating the SAR problems illustrated in FIG. 5. That is, by simply stretching or lengthening both the gradient waveform 216 and the RF pulse shape 218, SAR can be reduced and the flip angle distribution can be maintained. However, such an approach as a design solution would be undesirable due to the increased duration of the pulse 218. As shown, gradient waveform 216 has been approximately doubled in duration and halved in amplitude, compared to the gradient waveform shown in FIG. 5. Likewise, the RF pulse 218 of FIG. 6 has also been approximately doubled in duration and halved in amplitude, compared to the RF pulse of FIG. 5. FIG. 6 also illustrates that the slew rate 214 of the gradient waveform 216, while remaining constant, has been substantially reduced due to the slower oscillations of gradient waveform 216. Therefore, it can be seen that under certain circumstances, reducing slew rate may, in effect, correlate to a reduction in SAR.

Figure 7:
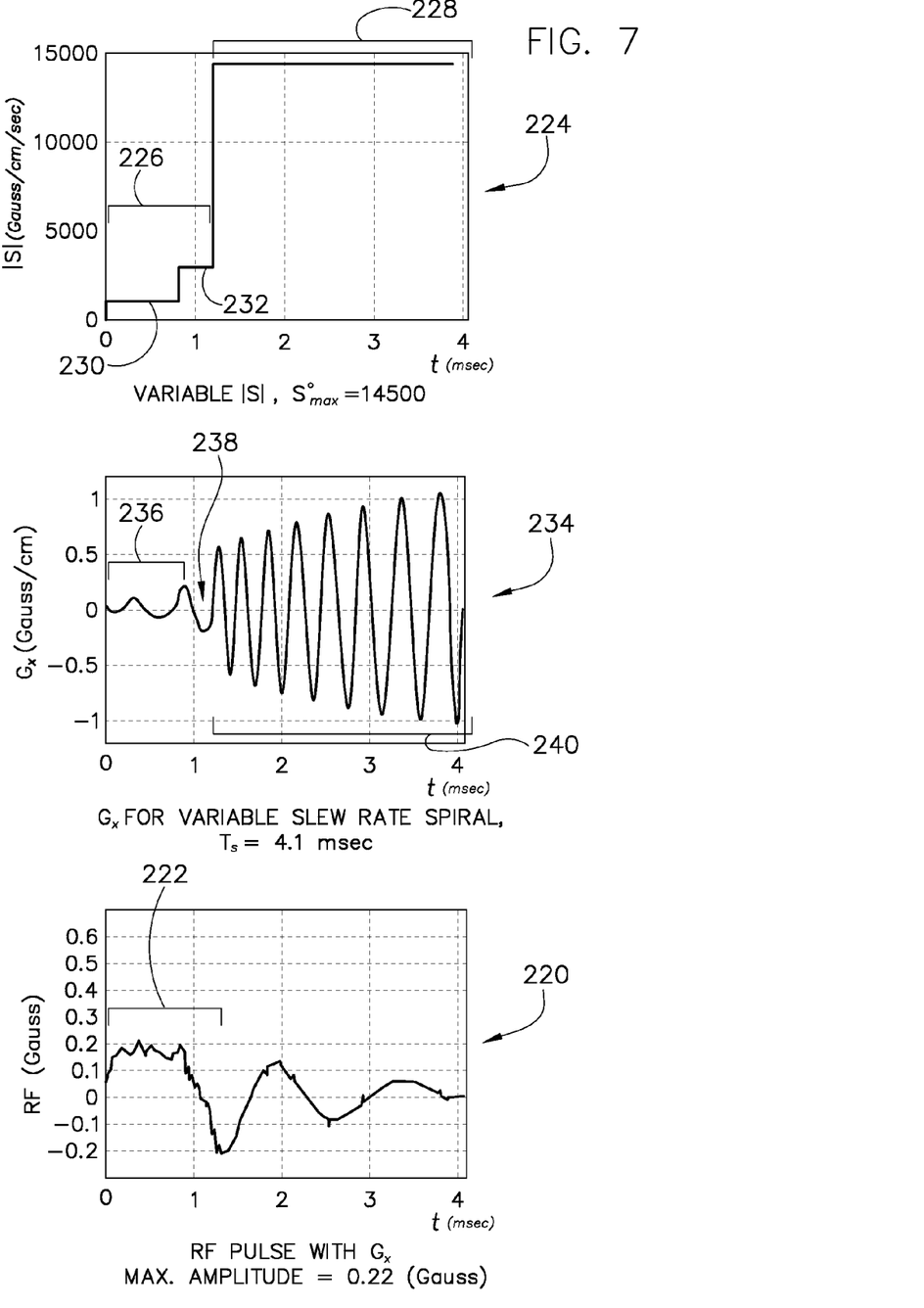
FIG. 7 is a graph of an exemplary, variable slew rate with a corresponding frequency encoding gradient and RF waveform.

FIG. 7 depicts another technique for reducing SAR in multi-dimensional spatially selective RF pulses associated with non-Cartesian k-space trajectories. The technique represented in FIG. 7 shall be referred to herein as a variable slew rate design. As can be seen, RF pulse 220 has been adjusted to reduce peak RF power. That is, the segment 222 of RF pulse 220 corresponding to the peak portion 214 of FIG. 5 has been reduced in amplitude and lengthened in duration, in order to maintain the effective flip angle for segment 222. Thus, it can be understood that similar adjustments are made to the gradient waveform 234 of FIG. 7. However, the adjustments to gradient waveform 234 avoid the problems described with respect to FIG. 2.

To effectuate a smooth transition between a reduced and lengthened segment of an oscillating gradient waveform and the remainder of such a waveform, a maximum allowable slew rate function can be determined. By dynamically varying the maximum slew rate used by the oscillating gradient waveform 234, non-implementable discontinuities in the waveform can be avoided. As shown in FIG. 7, a maximum allowable slew rate 224 is plotted. Initially, the maximum slew rate is held to a lower value 230. Prior to resuming the maximum slew rate at segment 228, the allowable slew rate function 224 briefly varies the maximum slew rate to an intermediate value 232. For other RF pulses and/or k-space trajectories, the allowable slew rate function might have a linearly increasing initial segment, followed by a constant segment at the maximum slew rate. As will be discussed below, the allowable slew rate function may be calculated depending upon the desired RF pulse profile and the k-space trajectory. The gradient waveform 234 resulting from application of the maximum allowable slew rate function exhibits no major discontinuities at portion 238. That is, gradient waveform 234 has a lowest slew rate portion 236, an intermediate portion 238, and an unchanged or maximum slew rate segment 240. Accordingly, the gradient waveform 234 can be implemented by most gradient coils and amplifiers.

A variable slew rate gradient waveform approach, such as illustrated in FIG. 7, indirectly reduces gradient amplitude of both the Gx and Gy gradients which are played out during 2D RF pulse transmission, and therefore reduces total $B_1$ power. By reducing the maximum allowable slew rate for portions of increasing oscillating gradient waveforms corresponding to a high amplitude RF transmission, the increasing oscillating gradient waveforms are, in effect, lengthened in duration and held at lower amplitudes. The remaining portion of the increasing oscillating gradient waveforms is permitted to utilize the full available maximum slew rate, and therefore remain mostly unchanged from typical design techniques. A mathematical definition of a variable slew-rate spiral and solutions to its gradient waveforms are given below.

To begin, a definition for an exemplary spiral k-space trajectory is given by:

$$k(t)=\lambda\theta(t)e^{i\theta(t)} \qquad \text{Eqn. 1,}$$

where $\lambda=N_{int}/D$ is a constant that determines the radial sampling interval, with $N_{int}$ being the number of interleaves or turns of the spiral and D being the size of the field-of-view. $\theta(t)$ is the azimuthal angle of the k-space trajectory, k(t), in polar coordinates. Therefore, the corresponding gradient waveform can be determined form the following:

$$G(t) = \frac{\lambda}{\gamma}\dot{\theta}(t)(1 + i\theta(t))e^{i\theta(t)}, \qquad \text{Eqn. 2}$$

in which $\dot{\theta}(t)$ denotes the derivative of $\theta(t)$. The complex slew rate for a gradient determined according to Eqn. 2 can be found from:

$$S(t) = \frac{\lambda}{\gamma}\left[\ddot{\theta}(t) - \theta(t)\dot{\theta}^2(t) + i\left(\theta(t)\ddot{\theta}(t) + 2\dot{\theta}^2(t)\right)\right]e^{i\theta(t)}, \qquad \text{Eqn. 3}$$

in which $\ddot{\theta}$ denotes the second derivative of $\theta(t)$. The magnitudes of the gradient waveform and slew rate given by Eqns. 2 and 3 are:

$$|G(t)| = \frac{\lambda}{\gamma}\dot{\theta}(t)(1 + \theta^2(t))^{1/2}, \qquad \text{Eqn. 4}$$

$$|S(t)| = \frac{\lambda}{\gamma}\left[\left(\ddot{\theta}(t) - \theta(t)\dot{\theta}^2(t)\right)^2 + \left(\theta(t)\ddot{\theta}(t) + 2\dot{\theta}^2(t)\right)^2\right]^{1/2}. \qquad \text{Eqn. 5}$$

For hardware limitations, we denote the maximum gradient amplitude as $G_{max}$, the maximum slew-rate as $S°_{max}$, and the maximum $B_1$ amplitude as $B_{max}$. For a variable slew-rate spiral, $|S(t)|$ is subjected to a time-varying maximum allowable slew-rate $S_{max}(t)$ constraint, upper bounded by $S°_{max}$.

Since it is frequent that not all portions of an RF pulse $B_1(t)$ exceed $B_{max}$, the slew rate of a gradient waveform may be varied only where the net $B_1(t)$ exceeds $B_{max}$, while remaining portions of the gradient waveform can maintain the maximum slew rate, $S°_{max}$. For example, after designing a constant slew-rate spiral trajectory with a slew rate constraint of $S°_{max}$ and the corresponding RF pulse, the constant slew rate profile may be locally scaled to a maximum allowable slew rate function, $S_{max}(t)$. $S_{max}(t)$ may be set to $S°_{max}$ where $B_1(t)$ does not exceed $B_{max}$, and to a scaled $S°_{max}$ where $B_1(t)$ does exceed $B_{max}$ (with the corresponding time scaling).

Mathematically, $S_{max}(t)$ can be written as:

$$S_{\max}(t) = \frac{S_{\max}^{\circ 2}}{\eta^2(\varphi^{-1}(t))}, \quad \text{Eqn. 6}$$

where $\varphi^{-1}(t)$ is the inverse function of the time-warping function $\varphi(t)$:

$$\varphi(t) = \int_0^t \eta(\tau) d\tau \quad \text{Eqn. 7}$$

and $\eta(t)$ is the amplitude scaling function. It is to be noted that $\varphi(t)$ is different from the time dilation function in VERSE in that $\varphi(t)$ directly operates on a slew-rate waveform. Thus, it is relatively straightforward to ensure that a slew-rate does not violate $S°_{max}$. In contrast, the dilation function in VERSE operates on the gradient waveform itself. Moreover, the choice of $\eta(t)$ in the variable slew rate technique can be relatively flexible.

One way to choose $\eta(t)$ is:

$$\eta(t) = \begin{cases} 1 & \text{if } B_1(t) \leq B_{\max} \\ \lceil B_1(t)/B_{\max} \rceil & \text{otherwise} \end{cases} \quad \text{Eqn. 8}$$

where $\lceil x \rceil$ denotes a round-up of x to the nearest integer, which may be done to avoid interpolation error from fractional values. The form of $\eta(t)$ in Eqn. 8 may be rather jagged, which would translate to an undesirably jagged RF pulse waveform. Therefore, some embodiments include a "smoothed" version of Eqn. 8, such as one based on a piecewise constant or linear model. For example, one way to generate a piecewise constant $\eta(t)$ is to assign a unity value in regions where $B_1(t) \leq B_{max}$, then divide the regions where $B_1(t) > B_{max}$ into sections and assign a constant value to each section, with the constant being the maximum $\lceil B_1(t)/B_{max} \rceil$ of that section.

Accordingly, it is to be appreciated that a variable slew-rate spiral design is not strictly equivalent to local scaling. The shape of $\eta(t)$ (e.g., the amplitude of a particular segment in a piecewise constant model) and thus $S_{max}(t)$ may be adjusted through a few iterations to obtain the desired RF pulse waveform. In some embodiments, 1 to 4 iterations are usually sufficient to obtain a $S_{max}(t)$ function that gives the desired RF pulse waveform.

When a non-Cartesian k-space trajectory is long enough to have a gradient amplitude limited region, it may be desirable to ensure that $|G(t)|$ stays at $G_{max}$ once reaching it. To do so, $S_{max}(t)$ can be maintained at a sufficiently high value during the gradient amplitude limited case. This condition can be met by ensuring that $S_{max}(t)$ reaches $S°_{max}$ before the gradient waveform reaches the gradient amplitude limited segment and then ensuring that $S_{max}(t)$ remains at $S°_{max}$ thereafter. This will often be the case, because the gradient amplitude limited segment of a gradient waveform for a spiral k-space trajectory occurs near the end of the waveform, corresponding to the periphery of k-space. Thus, in such an instance there would be no need to reduce the maximum allowable slew-rate to lower gradient and RF pulse amplitudes.

Given an $S_{max}(t)$, and following a derivation similar to that for a constant slew-rate spiral, a pair of differential equations for designing the gradient waveforms of a variable slew-rate spiral trajectory are as follows:

$$\ddot{\theta}(t) = \frac{f(\theta(t), \dot{\theta}(t)) - \theta(t)\dot{\theta}^2(t)}{1 + \theta^2(t)}, \quad \text{Eqn. 9}$$

where $$f(\theta(t), \dot{\theta}(t)) = \begin{cases} \left[ (\gamma S_{\max}(t)/\lambda)^2(1 + \theta^2(t)) - \dot{\theta}^4(t)(2 + \theta^2(t))^2 \right]^{1/2} & \text{if } |G(t)| < G_{\max} \\ 0 & \text{otherwise} \end{cases} \quad \text{Eqn. 10}$$

Equations 6 and 7 can be solved by standard numerical methods with boundary conditions of $\theta(0)=0$ and $\dot{\theta}(0)=0$. Normally, gradient waveforms which implement spiral k-space trajectories will oscillate at the maximum slew rate before the gradient magnitudes reach $G_{max}$, as shown in FIG. 5, for example. Once the amplitude of the waveforms increases to the maximum available gradient strength, $G_{max}$, the waveforms will stop increasing in amplitude and the slew rate will drop some amount.

Another way to solve for $S_{max}(t)$ is by using an analytical approach. In instances in which fast calculation of gradient waveforms is required or the k-space trajectory has a relatively high number of spiral turns, an analytical solution may be desirable. First, an analytical solution for the segment of a gradient waveform limited by the slew rate is presented. For $\theta(t) \gg 1$, Eqn. 5 becomes:

$$\theta(t)\dot{\theta}^2(t) \approx \gamma S_{max}(t)/\lambda \quad \text{Eqn. 11.}$$

Solving Eqn. 11 yields:

$$\lim_{t \to \infty} \theta(t) = \alpha(P(t))^{2/3}, \quad \text{Eqn. 12}$$

$$\alpha = \left( \frac{9\gamma S_{\max}^\circ}{4\lambda} \right)^{1/3}, \quad \text{Eqn. 13}$$

$$P(t) = \int_0^t \left( \frac{S_{\max}(\tau)}{S_{\max}^\circ} \right)^{1/2} d\tau. \quad \text{Eqn. 14}$$

At small t ($t \to 0$), Eqn. 12 does not hold because $\theta(t)$ is close to zero. Thus, for t=0 in Eqn. 5, applying the boundary conditions $\theta(0)=0$ and $\dot{\theta}(0)=0$ yields:

$$\ddot{\theta}(0) = |S(0)|\gamma/\lambda \leq S_{max}(0)\gamma/\lambda \equiv \beta \quad \text{Eqn. 15,}$$

which can be used to solve Eqn. 11 for:

$$\lim_{t \to 0} \theta(t) = q\beta t^2/2, \quad \text{Eqn. 16}$$

where q is a user defined constant between 0 and 1. Selecting different q values can affect the shape of resulting maximum allowable slew rate functions and gradient waveforms. Slew rate magnitude $|S(t)|$ curves corresponding to larger q values ramp up to the prescribed $S_{max}(t)$ faster, but initially overshoot the target S(t) more than curves corresponding to lower q values. Such an overshoot, however, is unlikely to violate the actual hardware limit $S°_{max}$ because the prescribed $S_{max}(t)$ in the initial gradient waveform segments is normally significantly smaller than $S°_{max}$. In contrast, |S(t)| curves corresponding to smaller q values do not overshoot or only slightly overshoot the prescribed $S_{max}(t)$, but the ramping is slower, which can increase the total length of gradient waveform slightly. Using values such as q=0.4 to 0.6 is suitable for 2D RF pulse design in terms of producing predictable RF amplitude drops without significantly increasing the pulse length. Therefore, in the general case, slew rate limited gradient waveforms (or segments thereof) can be found according to:

$$\theta_1(t) = \frac{\frac{\beta}{2}t^2}{\frac{1}{q} + \frac{\beta t^2}{2\alpha(P(t))^{2/3}}}.$$  Eqn. 17

Equations 9 and 13 generally hold true where P(t) is approximately equal to $t^n$, where n<3, for t→0 and t→∞. Thus, $S_{max}(t)$ is about $t^m$, where m<4, for t→0 and t→∞. These conditions may be satisfied by including terms up to the quadratic in $S_{max}(t)$. The gradient waveform for the slew rate limited case can therefore be obtained by replacing θ(t) in Eqn. 2 with $\theta_1(t)$ in Eqn. 17. The total time or duration of the gradient waveform, if the entire waveform is slew rate limited, can be determined by solving Eqn. 17 for $$t = T_s = \frac{N\pi}{N_{int}},$$

where N is the desired matrix size.

For longer gradient waveforms that have both slew rate limited segments and gradient amplitude limited segments, the time $t_s$ at which the waveforms transition between the segments can also be calculated. In other words, $t_s$ is the time for |G(t)| to reach $G_{max}$ when the gradient runs at $S_{max}(t)$ all the way until $|G(t)|=G_{max}$, and can be found according to:

$$G_{max} = |G(t_s)|$$  Eqn. 18
$$= \frac{\lambda}{\gamma}\dot\theta(t)(1+\theta^2(t))^{1/2}$$
$$\approx \frac{\lambda}{\gamma}\dot\theta(t)\theta(t)$$
$$= \frac{2\lambda}{3\gamma}(P(t_s))^{1/3}\left(\frac{S_{max}(t_s)}{S°_{max}}\right)^{1/2}.$$

The segment of a gradient waveform limited by the maximum achievable gradient strength can be calculated upon the assumption that $S_{max}(t)$ has reached $S°_{max}$. This will be the case, for non-Cartesian trajectories like spiral trajectories, after time $t_s$. Accordingly, the gradient amplitude segment of a waveform can be determined by:

$$\theta_2(t) = \left[\theta_s^2 + \frac{2\gamma}{\lambda}G_{max}(t-t_s)\right]^{1/2}, t_s \le t \le t_a,$$  Eqn. 19 where $\theta_s \equiv \theta_1(t_s)$ and the end time $t_a$ is given by:

$$t_a = t_s + \frac{\lambda}{2\gamma G_{max}}\left[\left(\frac{\pi N}{N_{int}}\right)^2 - \theta_s^2\right].$$  Eqn. 20

Accordingly, Equations 14 and 16 can be simplified and summarized for the general case of a variable slew rate gradient waveform design:

$$G(t) = \begin{cases} \frac{\lambda}{\gamma}\dot\theta_1(t)(1+i\theta_1(t))e^{i\theta_1(t)}, & 0 \le t \le t_s \\ G_{max}(1/\theta_2(t)+i)e^{i\theta_2(t)}, & t_s \le t \le t_a. \end{cases}$$  Eqn. 21

When $T_s<t_s$, a waveform will be only slew rate limited, and when $T_s>t_s$, a waveform will have a slew rate limited segment and a gradient amplitude limited segment.

Figure 8:
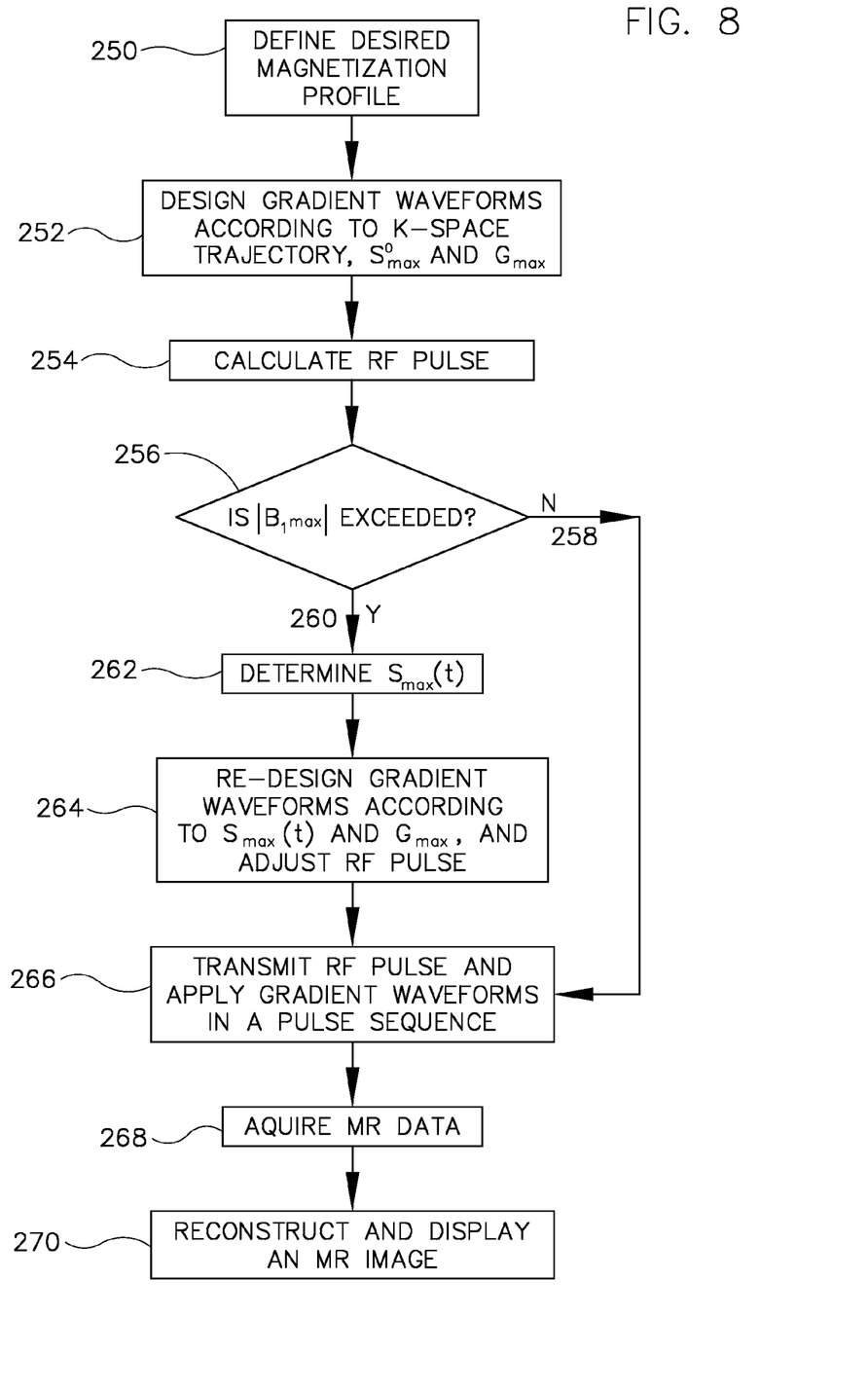
FIG. 8 is a flow chart setting forth an implementation of a variable slew rate design technique.

In practice, the variable slew rate design technique can be implemented in a variety of instances. Referring now to FIG. 8, the steps of an exemplary practical implementation of the variable slew rate design technique are shown. First, a user specifies the desired magnetization to be effectuated at block 250. At a user workstation or system control of an MR system, a user may graphically, textually, or numerically describe the magnetization itself, or may specify a number of parameters which indicate the desired magnetization, such as the desired pulse sequence, the RF pulse type, the desired k-space trajectory, the desired pulse sequence type, the FOV, the desired resolution, the desired flip angle, and the like. For example, a user may specify that a 2D spatially selective RF refocusing pulse for a 30 cm FOV is desired with a 20 turn single shot spiral trajectory. Next, the system designs gradient waveforms to implement an appropriate k-space trajectory, subject to $S°_{max}$ and $G_{max}$, at block 252. The type of k-space trajectory may be inferred based upon other user-specified parameters, or may be specifically selected by the user. Calculation of the gradient waveforms can also depend upon the field of view or excitation profile, the resolution, and other parameters. After the k-space trajectory has been determined, the RF pulse profile can be calculated at block 254. This calculation may be done according to a variety of known pulse design techniques, such as linear approximations.

Based upon user-defined or pre-selected SAR constraints, the system can determine at block 256 whether the magnitude of the $B_1$ field created by the gradient waveforms and RF pulse is too high. If the maximum B1 field strength is not exceeded 258, the system prepares for transmission at block 266. However, if the maximum B1 strength is exceeded 260, the system can begin making adjustments according to the variable slew rate design technique. At block 262, the system determines a maximum allowable slew rate function. In determining $S_{max}(t)$, the system may use a default q value, or may prompt the user textually or graphically to select a desired q value. Once the maximum allowable slew rate function has been determined, the system will then re-design the gradient waveforms accordingly at block 264. Depending upon the extent of the RF pulse that exceeds the maximum desired $B_1$, at least a portion of the gradient waveforms will reflect a varying slew rate. Correspondingly, the high amplitude portion of the RF pulse may also be adjusted by reducing the amplitude and lengthening that portion of the pulse.

After the RF pulse and gradient waveforms have been satisfactorily adjusted to conform to $B_1$ and/or SAR limitations, the RF pulse and gradient waveforms may be generated during a pulse sequence to excite spins of interest at block

268. The resulting MR signals detected by the MR system are acquired and at least temporarily stored as MR data at block 268. The system then reconstructs and MR image from the data according to a known reconstruction technique, and displays the image to the user at block 270.

Therefore, it has been shown that embodiments of the invention can provide implementable amplitude reductions in RF pulses which have associated non-Cartesian k-space trajectories. By controlling the allowable slew rate of the gradient waveforms applied during transmission of the RF pulse, the amplitude of the gradient waveforms can be indirectly limited. A complimentary reduction and stretching of the RF pulse may also be performed. Thus, in implementation, a realized technical effect of embodiments the present invention is the ability to provide selective control of $B_1$ strength when non-Cartesian k-space trajectories are employed.

Accordingly, in one embodiment of the present invention, an MR system includes a plurality of gradient coils positioned about a bore of a magnet, an RF transceiver system and switch controlled by a pulse module to transmit RF signals to an RF coil assembly to acquire MR images, and a controller operatively connected to the pulse module. The controller is programmed to determine an RF pulse profile and identify a high amplitude segment thereof. The controller is also programmed to design at least one gradient waveform, such that its slew rate varies in order to reduce $B_1$ field magnitude during transmission of the high amplitude segment of the RF pulse profile. The controller then outputs the RF pulse profile and the gradient waveform for transmission by the RF coil assembly and at least one of the gradient coils, respectively.

Another embodiment of the present invention includes a method for RF pulse amplitude reduction. At least one gradient waveform for a non-Cartesian k-space trajectory is designed. A maximum slew rate function is then determined to vary the slew rate of the gradient waveform during at least a portion of the slew-rate limited segment thereof. The gradient waveform is then re-designed according to the maximum slew rate function and is played out with an RF pulse to acquire MR image data. The MR image data is then at least temporarily stored.

In accordance with a further embodiment of the invention, a computer-readable storage medium has a particular set of instructions stored thereon. When the instructions are executed by a computer, the computer is caused to determine an allowable slew rate function and re-design an oscillating gradient waveform in accordance therewith. The instructions then cause the computer to output the oscillating gradient waveform and an RF pulse profile for transmission in an imaging sequence. Upon receipt of MR data resulting from the imaging sequence, the computer is caused to reconstruct and display an image based upon the MR data.

The present invention has been described in terms of the preferred embodiment, and it is recognized that equivalents, alternatives, and modifications, aside from those expressly stated, are possible and within the scope of the appending claims.

What is claimed is:

1. A magnetic resonance (MR) imaging apparatus comprising:
    a plurality of gradient coils positioned about a bore of a magnet;
    an RF transceiver system and switch controlled by a pulse module to transmit RF signals to an RF coil assembly to acquire MR images; and
    a controller operatively connected to the pulse module and programmed to:
        determine an RF pulse profile;
        identify a high amplitude segment of the RF pulse profile;
        design at least one gradient waveform, wherein a slew rate of the gradient waveform is dynamically varied throughout the gradient waveform to reduce a $B_1$ field magnitude during transmission of the high amplitude segment of the RF pulse profile; and
        output the RF pulse profile for transmission by the RF coil assembly and output the at least one gradient waveform for transmission by at least one of the plurality of gradient coils.

2. The MR imaging apparatus of claim 1 wherein the RF pulse profile is a multi-dimensional spatially-selective RF pulse profile.

3. The MR imaging apparatus of claim 2 wherein the high amplitude segment of the RF pulse profile occurs near a temporal beginning of the profile and corresponds to a central region of k-space.

4. The MR imaging apparatus of claim 1 wherein the controller is further programmed to design the at least one gradient waveform to have a time varying slew rate during a slew rate limited portion of the at least one gradient waveform.

5. The MR imaging apparatus of claim 4 wherein the gradient waveform is an oscillating gradient waveform and the controller is further programmed to design the oscillating gradient waveform to have a reduced slew rate, below a maximum slew rate, to maintain a low amplitude of the oscillating gradient waveform.

6. The MR imaging apparatus of claim 1 wherein the controller is programmed to design a preliminary gradient waveform to implement a spiral k-space trajectory in order to determine the RF pulse profile, then design the at least one gradient waveform as a re-design of the preliminary gradient waveform.

7. The MR imaging apparatus of claim 1 wherein the controller is further programmed to determine the gradient waveform to implement a spiral k-space trajectory.

8. A method for reducing RF pulse amplitude comprising:
    designing at least one gradient waveform to implement a non-Cartesian k-space trajectory;
    determining a maximum slew rate function to vary a gradient slew rate during at least a portion of a slew-rate limited segment of the at least one gradient waveform; wherein the slew-rate limited segment corresponds to a maximum amplitude segment of the RF pulse;
    re-designing the at least one gradient waveform according to the maximum slew rate function such that a $B_1$ field magnitude is reduced during transmission of the maximum amplitude segment of the RF pulse;
    playing out the at least one re-designed gradient waveform with an RF pulse to acquire MR image data; and
    at least temporarily storing the MR image data.

9. The method of claim 8 wherein designing the maximum slew rate function includes designing a linearly increasing slew rate section and a constant slew rate section to occur during the slew-rate limited segment of the at least one gradient waveform.

10. The method of claim 8 wherein designing the maximum slew rate function includes designing a step-wise increasing slew rate section to occur during a gradient amplitude-limited segment of the at least one gradient waveform.

11. The method of claim 8 wherein the non-Cartesian k-space trajectory is a spiral trajectory.

12. The method of claim 8 further comprising reducing and stretching the maximum amplitude segment of the RF pulse to be generally coextensive with the portion of the slew-rate limited segment of the at least one gradient waveform.

13. The method of claim 8 wherein the maximum slew rate function is a time-varying maximum allowable slew rate profile.

14. The method of claim 13 wherein re-designing the at least one gradient waveform includes solving for the at least one gradient waveform based upon the time-varying maximum allowable slew rate profile, using at least one of a numerical approach and an analytical approach.

15. A computer-readable storage medium having a set of instructions stored thereon which, when executed by a computer, cause the computer to:
   determine an allowable slew rate function;
   re-design at least one oscillating gradient waveform according to the allowable slew rate function; wherein the slew-rate is varied throughout the at least one oscillating gradient waveform to reduce a B1 field magnitude during transmission of a high amplitude portion of an RF pulse profile;
   output the at least one oscillating gradient waveform and the RF pulse profile for transmission in an imaging sequence; and
   reconstruct and display an image based upon MR data resulting from the imaging sequence.

16. The computer-readable storage medium of claim 15 wherein the instructions further cause the computer to design the allowable slew rate function to effect a reduction in magnitude of at least one oscillating gradient waveform during a period corresponding to a high amplitude portion of the RF pulse profile.

17. The computer-readable storage medium of claim 15 wherein the instructions further cause the computer to initially design the at least one oscillating gradient waveform to implement a standard spiral k-space trajectory.

18. The computer-readable storage medium of claim 15 wherein the allowable slew rate function includes an increasing allowable slew rate section and a constant allowable slew rate section.

19. The computer-readable storage medium of claim 18 wherein the increasing allowable slew rate section corresponds in time to a high amplitude portion of the RF pulse profile.

20. The computer-readable storage medium of claim 15 wherein the RF pulse profile is a multi-dimensional spatially selective RF pulse profile.

* * * * *